(12) United States Patent
Brenguer et al.

(10) Patent No.: US 6,551,568 B2
(45) Date of Patent: Apr. 22, 2003

(54) PROCESS FOR THE PREPARATION OF HYDRAZINE

(75) Inventors: Georges Brenguer, La Barthe de Neste (FR); Rémi Jullin, Lannemezan (FR); Jean-Philippe Ricard, Pau (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/826,665

(22) Filed: Apr. 5, 2001

(65) Prior Publication Data

US 2002/0016507 A1 Feb. 7, 2002

Related U.S. Application Data

(63) Continuation of application No. PCT/FR99/02217, filed on Sep. 17, 1999.

(30) Foreign Application Priority Data

Oct. 13, 1998 (FR) .............................................. 98 12781

(51) Int. Cl.[7] ....................... C01B 21/16; C07C 241/00; C07C 241/02
(52) U.S. Cl. ....................................... 423/407; 564/249
(58) Field of Search ........................... 564/249; 423/407

(56) References Cited

U.S. PATENT DOCUMENTS 5,252,309 A 10/1993 Krempf et al.
5,986,134 A * 11/1999 Kuriyama et al. .......... 564/249

FOREIGN PATENT DOCUMENTS

AU 5576690 11/1990

* cited by examiner

Primary Examiner—Wayne A. Langel
(74) Attorney, Agent, or Firm—Pennie & Edmonds LLP

(57) ABSTRACT

Process for the preparation of azine and of hydrazine by bringing ammonia, hydrogen peroxide and a reactant carrying a carbonyl group into contact with a working solution, comprising:

the treatment of an aqueous stream resulting from the circuit for the regeneration of the said working solution with an amount of acid such that the pH of the said stream is brought to a value of less than 6.4, then the recycling of the said stream in the reactor for the synthesis of the azine.

17 Claims, 3 Drawing Sheets

PROCESS FOR THE PREPARATION OF HYDRAZINE

This is a continuation of application No. PCT/FR99/02217, filed Sep. 17, 1999.

The subject-matter of the present invention is a process for the preparation of azine and a process for the preparation of hydrazine employing it.

The synthesis of hydrazine from ammonia and hydrogen peroxide is described in Ullmann's Encyclopedia of Industrial Chemistry (1989), Vol. A 13, pages 182–183.

In a first stage, ammonia, hydrogen peroxide and a reactant carrying a carbonyl group are reacted in a reactor in order to form an azine, according to the reaction (I):

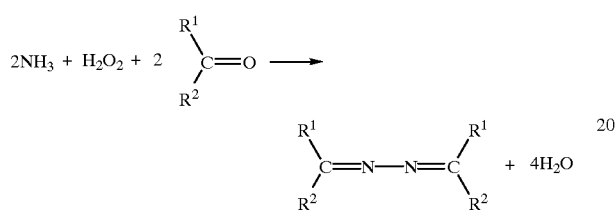

In this scheme, $R^1$ and $R^2$, which are identical or different, represent a hydrogen atom or a $C_1$–$C_4$ alkyl radical, provided that at least one of $R^1$ and $R^2$ is other than a hydrogen atom, or else $R^1$ and $R^2$ form, together with the carbon atom to which they are bonded, a $C_3$–$C_6$ cycloalkyl radical.

This reaction is necessarily carried out in the presence of a catalyst (or activator) or of a mixture of catalysts included within a composition denoted as working solution. At the end of the reaction, the azine is separated from the working solution. The latter is then regenerated and then recycled in the reactor of Stage (I).

In a second stage, the azine is hydrolysed to hydrazine, according to the reaction (II):

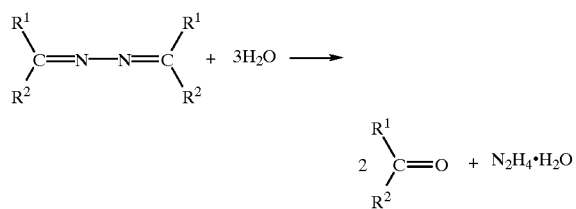

the reactant carrying a carbonyl group is recovered and recycled in the reactor of Stage (I).

This process was disclosed in particular in U.S. Pat. Nos. 3,972,878 and 3,972,876.

The term "working solution" is therefore understood to mean any aqueous solution or suspension comprising a catalyst or a mixture of catalysts which is capable of converting a mixture of ammonia, of hydrogen peroxide and of a reactant carrying a carbonyl group to an azine.

This working solution is disclosed in Patents EP 399,866, EP 487,160 and EP 70,155. It is composed, for example, of an aqueous solution of acetamide and of ammonium acetate. The ammonium acetate is formed in the reactor, in particular by reaction of acetic acid with ammonia. The working solution can also be composed of an aqueous solution of cacodylic acid and of ammonium cacodylate.

Application EP 0,518,728 discloses a process for the synthesis of azine in which the working solution and more generally any stream entering the reactor for the synthesis of the azine are devoid of $CO_2$. According to this application, the presence of $CO_2$ in the synthesis process generally results from undesirable reactions of the hydrogen peroxide with various organic impurities which are produced in certain stages of the process. The $CO_2$ thus formed reacts in its turn with the hydrogen peroxide, which results in an excessive consumption of $H_2O_2$ and a fall in the yield of azine intermediate and thus of hydrazine.

To overcome this disadvantage, Application EP 0,518,728 discloses a process for the preparation of intermediate azine, in which a) ammonia, hydrogen peroxide and a reactant carrying a carbonyl group are brought into contact in a reactor with a working solution, then b) the azine thus formed is separated from the working solution, then c) the working solution is regenerated by bringing it to a temperature of at least 130° C., so that the $CO_2$ and most of the water (formed during the reaction of Stage a) or contributed by the water of dilution of the hydrogen peroxide) are removed in the form of an aqueous stream, denoted C1 in the continuation of the present text, which therefore comprises, in the dissolved state, in addition to the $CO_2$ (essentially present in the carbonate form), a certain amount of the ammonia and of the reactant carrying a carbonyl group employed in Stage a), then d) the working solution, regenerated according to Stage c), is recycled in the reactor of Stage a).

The stream C1 comprises a certain amount of ammonia and of reactant carrying a carbonyl group. However, it cannot be directly recycled in the reactor for the synthesis of the azine, specifically because of the presence of a significant amount of $CO_2$. In order to economize on the significant amounts of reactants which can be used in the process, Application EP 0,518,728 therefore recommends complementing Stage d) of the said process by treating this stream C1 so as to remove the $CO_2$ therefrom, in order to be able thus to recycle the ammonia and the reactant carrying a carbonyl group which it comprises in the reactor for the synthesis of azine. FIG. 1/3 represents a device suited to the implementation of this process. It is described in a detailed way later in the present text, in the appropriate part.

A process for the treatment of the stream C1 appropriate for the removal of $CO_2$, such as the removal mentioned in Stage d), is also disclosed by Application EP 0,518,728.

According to this process, the stream C1 is first of all treated in a stripping column, the top stream of which is cooled in a condenser. The $NH_3$ is collected in the gaseous state, and the liquid phase obtained is separated, in a settling tank, into the organic phase, rich in reactant carrying a carbonyl group, and the aqueous phase.

The $NH_3$ and the organic phase thus obtained are recycled to the reactor for the synthesis of the azine.

The aqueous phase, which comprises all the $CO_2$ present in the stream C1, is fed to a 2nd distillation column, so as to collect:

at the column top, an aqueous stream devoid of $CO_2$ and comprising a certain amount of ammonia and of reactant carrying a carbonyl group, which is therefore recycled to the reactor for the synthesis of the azine, at the column bottom, an aqueous stream, denoted C2 in the continuation of the present text, which comprises virtually all the $CO_2$ present in C1 and also small amounts of ammonia and of reactant carrying a carbonyl group.

FIG. 2/3 represents, as a reminder, the device taught by EP 518, 728 for the treatment of the stream C1.

Under the practical conditions of implementation of the process, the Stream C2 generally comprises from 0.1 to 20% by weight of $CO_2$ (present in the form of carbonate in the dissolved state), from 1 to 15% of $NH_3$ and from 0.1 to 10% of reactant carrying a carbonyl group.

In the present text, except when otherwise indicated, the percentages shown for the components are percentages expressed by weight.

Application EP 0,518,728 gives no teaching relating to the treatment to be given to the Stream C2. According to this application, it cannot be recycled to the reactor for the synthesis of the azine, since it comprises $CO_2$.

The removal of such a Stream C2 might be envisaged by means of known techniques, such as incineration. However, this removal would necessarily be accompanied by releases to the atmosphere of a mixture of compounds of the NO or $NO_2$ type, resulting from the combustion of $NH_3$. In point of fact, it is desirable to limit as far as possible the discharge to the atmosphere of such compounds. Furthermore, this removal would also involve the loss of small amounts of reactants which can be used in the process, namely ammonia and reactant carrying a carbonyl group, which loss is harmful to the economics of the process.

Application EP 0,518,728 suggests removing the $CO_2$ by washing with sodium hydroxide solution, in order to retain the $CO_2$ in the form of an aqueous sodium carbonate solution and to leave the ammonia, the reactant carrying a carbonyl group and water vapour in gaseous form.

A novel process for the preparation of the azine has now surprisingly been found which, in contrast to the teaching of Patent EP 0,518,728, involves an acid in the treatment of the Stream C2.

One aim of the invention is therefore to provide a process for the preparation of azine in which the discharges of effluents to the environment are reduced.

Another aim of the invention is to provide a process for the preparation of azine in which the losses of reactants of use in the reaction are reduced.

These aims can be achieved, in all or in part, by the process for the preparation of azine which is the subject-matter of the invention, which process is described hereinbelow.

The subject-matter of the invention is therefore, firstly, a process for the preparation of azine comprising the stages:

(i) in which, successively
  (a) ammonia, hydrogen peroxide and a reactant carrying a carbonyl group are brought into contact, in a reactor, with a working solution,
  (b) the azine thus formed is separated from the working solution,
  (c) the working solution is regenerated by bringing it to a temperature of at least 130° C., so that the $CO_2$ and most of the water (formed during the reaction of Stage a) or contributed by the water of dilution of the hydrogen peroxide) are removed in the form of an aqueous stream C1, which therefore comprises, in the dissolved state, in addition to the $CO_2$ (present essentially in the carbonate form), a certain amount of ammonia and of the reactant carrying a carbonyl group employed in Stage a),
  (d) the working solution, regenerated according to Stage c), is recycled in the reactor of Stage a); and
(ii) in which, successively
  (a) the said stream C1 is treated in a stripping column;
  (b) the top stream is condensed while separating the $NH_3$ in the gaseous state;
  (c) the liquid phase resulting from the condensation is separated into an organic phase, rich in reactant carrying a carbonyl group, and an aqueous phase comprising all the $CO_2$ present in C1;
  (d) the said aqueous phase is fed into a distillation column, from where an aqueous stream devoid of $CO_2$ is collected at the top and an aqueous stream C2 comprising virtually all the $CO_2$ present in C1 is collected at the bottom, characterized in that
  at least a portion of the stream C2 is treated with an amount of acid such that the pH of the said stream is brought to a value of less than 6.4, preferably less than 6 ; then
  the said portion (denoted stream C3) thus treated is recycled in the reactor of Stage (i)(a).

This process is particularly advantageous in that it makes it possible to recover most of the amounts of $NH_3$ and of reactant carrying a carbonyl group present in the stream C1, in order for them to be reused in the reactor for the synthesis of the azine. This results in an appreciable saving. Furthermore, in contrast to the treatment with sodium hydroxide solution suggested by EP 0,518,728, it makes it possible to avoid any problem of liquid or solid discharge to the environment, the $CO_2$ being removed by simple degassing.

The treatment with the acid is usually carried out at a temperature of between 20 and 70° C., preferably between 40 and 60° C., and at a pressure of between 0.5 and 4 bar absolute, preferably between 0.5 and 2 bar absolute.

The aqueous stream C2 employed usually has a $CO_2$ content of between 0.1 and 20%, preferably between 0.5 and 5%, an $NH_3$ content of between 1 and 15%, preferably between 1 and 6%, and a content of reactant carrying a carbonyl group of between 0.1 and 10%, preferably between 0.1 and 5%. The pH of the aqueous stream C2 is usually between 8 and 12.

It is preferable to subject the whole of the Stream C2 to the treatment with the acid.

It is also preferable to employ the process according to the invention while choosing methyl ethyl ketone as reactant carrying a carbonyl group. In this case, the corresponding azine is insoluble in aqueous solution, which facilitates Stage (i)(b) of separation of the azine from the working solution.

The acid employed in the treatment of the aqueous stream C2 is advantageously an acid with a $pK_a$ of less than 6.3, preferably of less than 5.

According to a preferred alternative form of the process according to the invention, the working solution employed comprises an aqueous solution of acetamide and of acetic acid. In this case, it is preferable to use acetic acid in the treatment of the Stream C2, as acid with a $pK_a$ of less than 6.3.

According to another preferred alternative form of the process according to the invention, the working solution employed comprises an aqueous solution of cacodylic acid and of ammonium cacodylate. In this case, it will be preferable to use cacodylic acid for the treatment of the Stream C2, as acid with a $pK_a$ of less than 6.3.

In all cases, the treatment by neutralization of the Stream C2 can be carried out in a very simple, more particularly preferred, way by use of the stream of acid introduced into the circuit for the regeneration of the working solution in order to compensate for the losses occasioned by the circulation and treatment of the solution. The treatment of the Stream C2, which is carried out using a reactant already employed in the process, is consequently very advantageous in economic terms.

Another subject-matter of the invention is a process for the preparation of hydrazine, comprising the process for the preparation of the azine as described above, in which the azine separated from the working solution in accordance with Stage (i) (b) of the said process is hydrolysed to hydrazine, the reactant carrying a carbonyl group being recovered and recycled in the reactor for the synthesis of the azine.

DETAILED DESCRIPTION OF THE FIGURES

Figure 1:
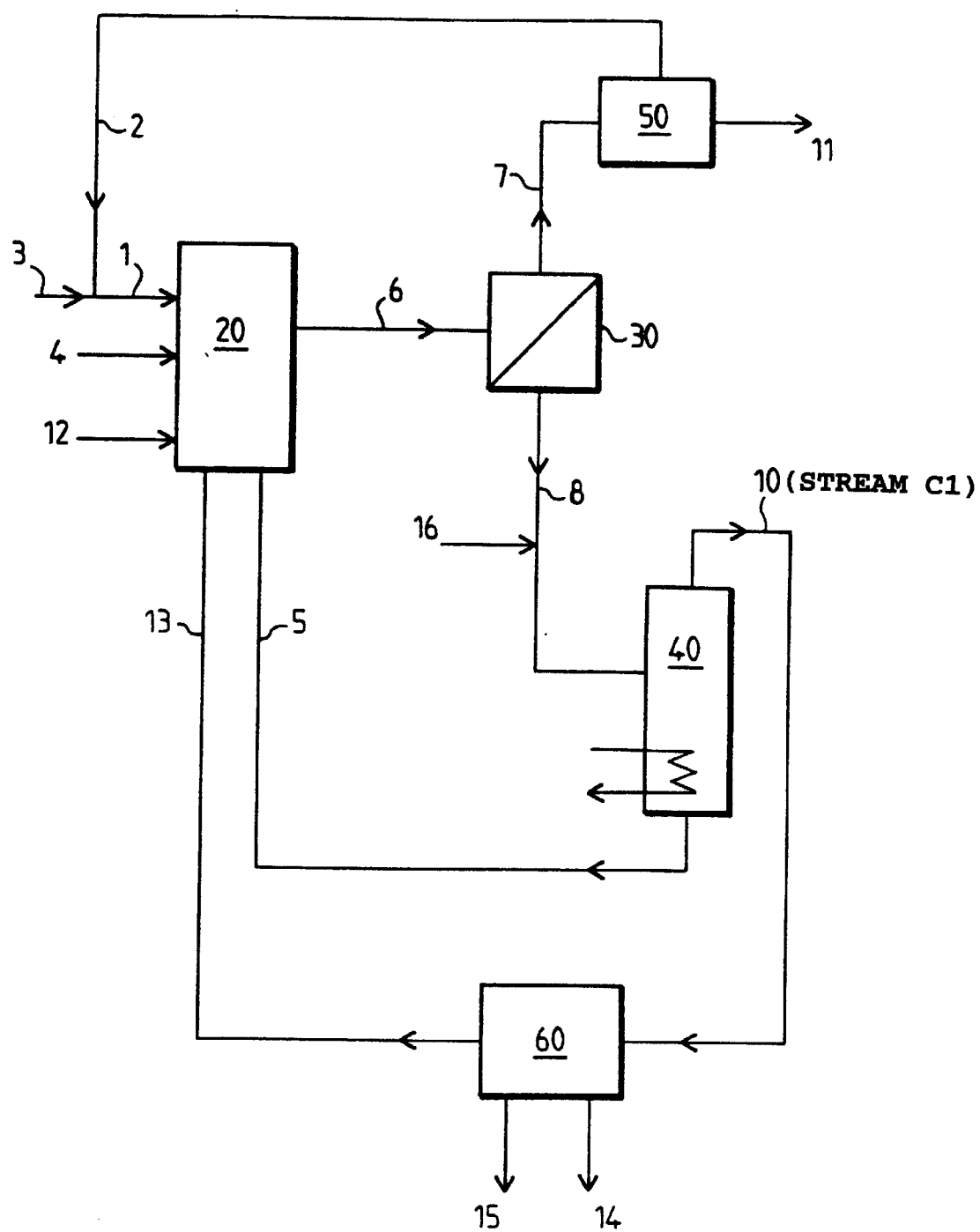
FIG. 1 represents a device for carrying out the synthesis of hydrazine from ammonia and hydrogen peroxide according to a process mentioned in EP 518,728.

FIG. 1/3:

FIG. 1/3 represents a device for carrying out the synthesis of hydrazine from ammonia and hydrogen peroxide according to a process mentioned in EP 518,728.

The azine is synthesized in the reactor 20. 1 represents the feed of reactant carrying a carbonyl group, composed of the recycling coming from the hydrolysis reactor 50 and of an optional makeup 3. 4 represents the feed of $NH_3$, 12 represents the feed of hydrogen peroxide and 5 represents the recycling of the working solution. The synthesis product is conveyed via a pipe 6 into the separator 30, which produces the crude azine at 7 and the working solution at 8, which working solution also comprises ammonia, a small amount of ketone, the water which is formed by reaction and the water which was contributed by the hydrogen peroxide, since, for reasons of safety, use is made of hydrogen peroxide at a concentration of at most 70% by weight in water.

The separator 30 can be a simple settling tank, if the azine is insoluble in the working solution and in the water of reaction; if not, a distillation column is used. The function of the working solution is to catalyse the synthesis of azines and to carry the water of reaction and the water contributed with the hydrogen peroxide via the pipe 8 to the device 40.

The working solution is brought in the device 40 to a temperature of at least 130° C. and preferably of between 150 and 250° C. A stream C1 comprising:

$CO_2$ in the form of ammonium carbonate, the water formed by the reaction and the water contributed by the hydrogen peroxide, ammonia, reactant carrying a carbonyl group, is recovered at 10.

The regenerated working solution, which comprises acetamide and acetic acid, is recovered at 5 and is returned to the reactor 20.

The stream 10 (stream C1) is conveyed to the treatment unit 60.

The following are obtained at the outlet of this unit 60:

a stream 13, corresponding to the combination of a gaseous $NH_3$ stream (stream 103 of FIG. 2/3), of a stream rich in MEK (stream 104 of FIG. 2/3) and of an aqueous stream comprising small amounts of $NH_3$ and MEK (stream 108 of FIG. 2/3); this stream 13 is recycled in the reactor 20 a stream of water 14, a stream 15 comprising the $CO_2$ present in the stream 10 and small amounts of $NH_3$ and of MEK.

The stream for the introduction of acetic acid 16 is provided in order to compensate for the losses occasioned by the circulation and the treatment of the working solution.

The azine is hydrolysed at 50 to hydrazine, which is drawn off at 11, and the ketone is recycled to the reactor 20 at 2.

FIG. 2/3

Figure 2:
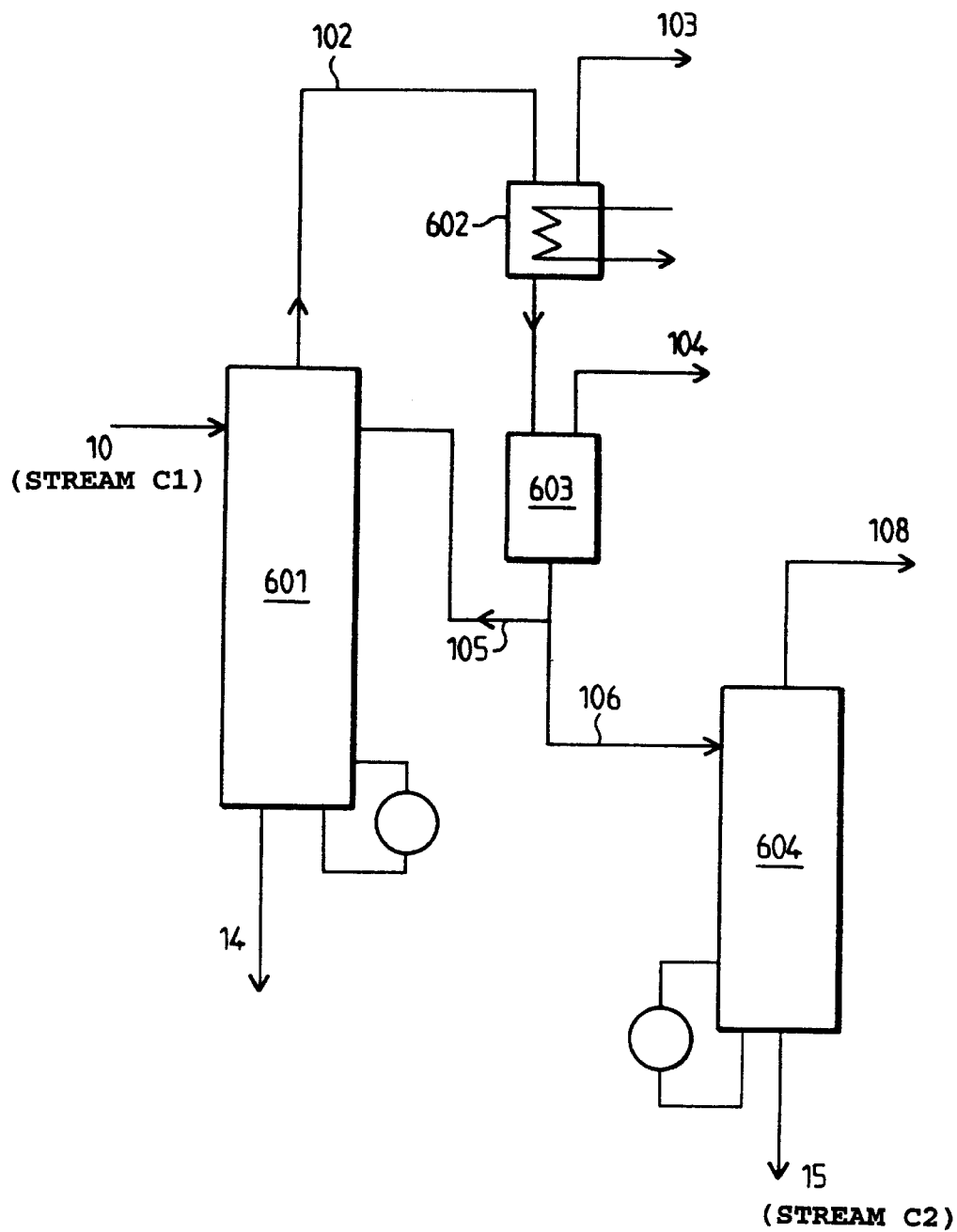
FIG. 2 represents the breakdown of the treatment carried out in the unit 60 of FIG. 1.

FIG. 2/3 represents the breakdown of the treatment carried out in the unit 60 of FIG. 1/3. This treatment is in accordance with a device taught by EP 518,728 for the treatment of the stream C1 corresponding to the stream 10 of FIGS. 1/3 and 2/3.

The stream C1, as defined above, arrives at the top of a stripping column 601 equipped with a reboiler. The $CO_2$ in 10 is in the form of ammonium carbonate. The water stream 14 is recovered at the bottom and a top stream 102 is recovered and is cooled to between 30 and 50° C. in a condenser 602. A portion of $NH_3$ does not condense and is recycled via a stream 103 to the reactor for the synthesis of the azine. The liquid phase passes into the tank 603.

Depending on the solubility of the reactant carrying a carbonyl group, it is possible to have an organic phase which is rich in this reactant. This is in particular the case for methyl ethyl ketone. This organic phase is recycled via a stream 104 to the reactor for the synthesis of the azine. The aqueous phase present in 603 comprises all the $CO_2$ (in the form of ammonium carbonate) which existed in the stream C1 (stream 10 in the figures). A portion 105 of this aqueous phase is conveyed to the column 601 as reflux and the stream 106 is flashed under low pressure in a column 604.

The bottom temperature of the column 604 is maintained between 20 and 45° C. by a reboiler and the pressure is maintained between $8 \times 10^3$ Pa (60 mm Hg) and $12 \times 10^3$ Pa (90 mm Hg) absolute by a vacuum pump or any equivalent device. The top stream 108 comprises ammonia and the reactant carrying a carbonyl group, and water. This stream is devoid of $CO_2$ and is therefore recycled to the reactor for the synthesis of the azine.

The stream C2 is the stream 15, obtained at the bottom of the column 604, which comprises all the $CO_2$ (in the form of ammonium carbonate) present in the stream C1, as well as water and small amounts of $NH_3$ and of reactant carrying a carbonyl group.

FIG. 3/3:

This figure illustrates an embodiment of the process according to the invention. In this figure, the treatment unit 60 is identical to that represented in FIG. 2/3. Only the differences from FIG. 1/3 are commented on hereinbelow.

The stream 15 (stream C2) resulting from the bottom of the column 604 is fed into a stirred reactor 70 maintained at 45° C., into which is introduced the stream 16 of acetic acid introduced in order to compensate for the losses occasioned by the circulation and treatment of the working solution.

The stream 17 represents the stream of $CO_2$ removed by degassing and the stream 18 represents the aqueous stream C3 comprising substantially no more $CO_2$ and comprising small amounts of $NH_3$ (in the form of ammonium acetate) and of MEK.

The following example is given purely by way of illustration of the present invention and should under no circumstances be interpreted as limiting the scope thereof.

EXAMPLE

Figure 3:
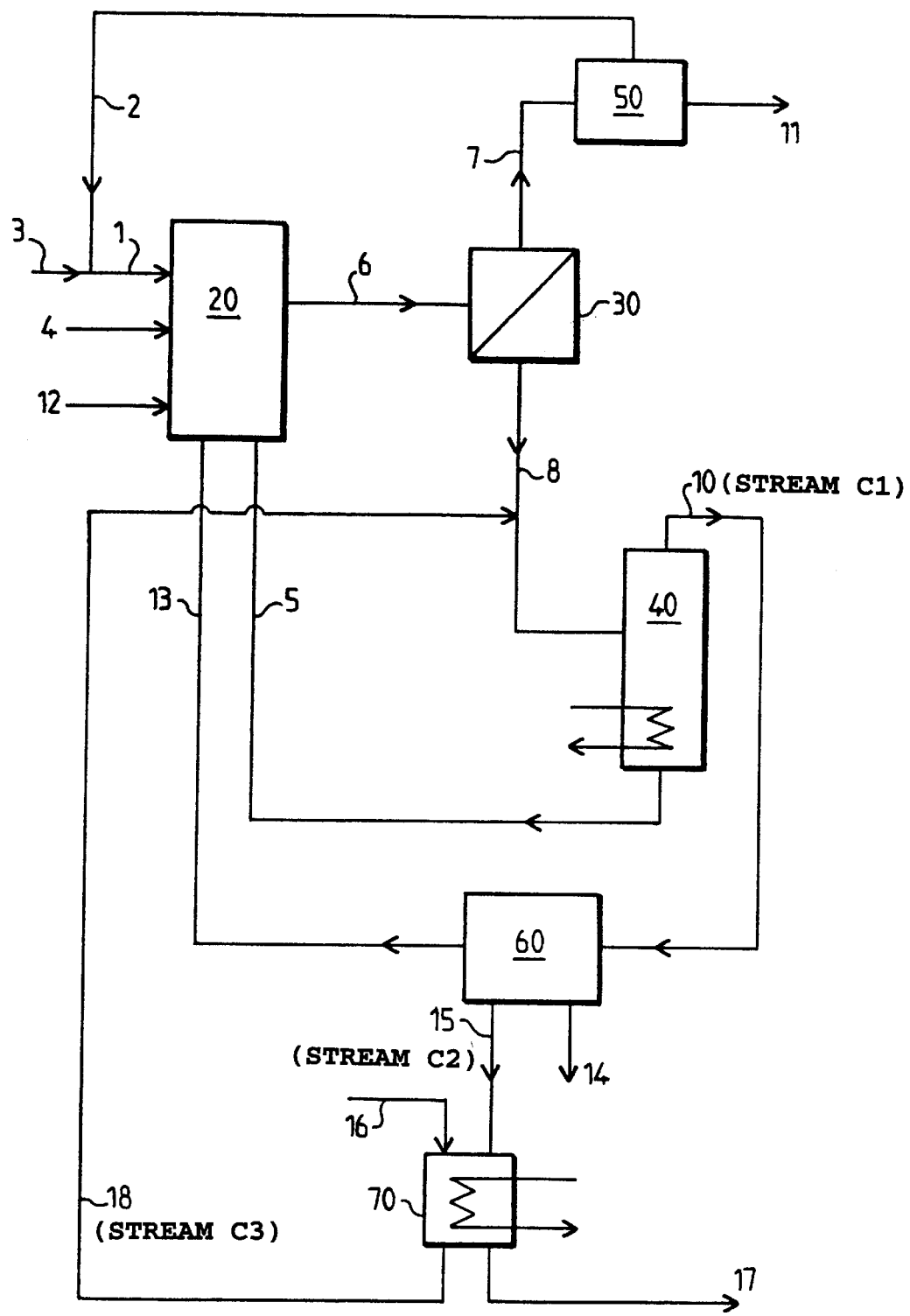
FIG. 3 illustrates an embodiment of the process according to the invention.

An azine is synthesized, by reaction of methyl ethyl ketone (MEK), ammonia and hydrogen peroxide in the presence of a working solution comprising acetamide and ammonium acetate, in accordance with FIGS. 2 and 3.

A stream 15 (stream C2) is obtained, with a throughput of 350 kg/h, which comprises the following compounds:

$CO_2$: 1.42% (expressed as molar equivalent weight of carbonate)

$NH_3$: 4%

MEK 1.5%

The pH of this stream is 10.4.

The stream 16, corresponding to the introduction of 75% acetic acid into the unit, is 150 kg/h. The whole of the stream 15 is introduced into the acidification reactor maintained at a temperature of 45° c.

At the outlet of the acidification reactor, a stream 18 (stream C3) is obtained with a throughput of 500 kg/h, with a pH of 5.5 and with a $CO_2$ content reduced to 0.6%, which comprises:

ammonium acetate: 12% acetic acid: 13%

MEK: 1%

This stream 18 is returned to the reactor for the synthesis of the azine 20 by introduction into the stream 8 of the circuit for the regeneration of the working solution.

What is claimed is:

1. A process for preparation of an azine comprising the stages:

(i) successively:
   (a) reacting ammonia, hydrogen peroxide and a reactant carrying a carbonyl group in a working solution in a reactor to form the azine,
   (b) separating the azine from the working solution,
   (c) heating the working solution at a temperature of at least about 130° C., so that the $CO_2$ and most of the water are removed in the form of an aqueous stream C1, wherein the stream C1 comprising $NH_3$;
   (d) recycling the working solution to Stage a); and (ii) successively:
   (a) bringing the stream C1 in a stripping column;
   (b) separating $NH_3$ in a gaseous state from the stream C1;
   (c) condensing the stream C1 in a liquid state and separating the condensed stream C1 into two phases, that is, an organic phase which is rich in reactant carrying a carbonyl group, and an aqueous phase comprising substantially all the $CO_2$ present in C1;
   (d) feeding the aqueous phase into a distillation column, and collecting an aqueous stream devoid of $CO_2$ at the top of the distillation column and an aqueous stream C2 comprising substantially all the $CO_2$ present in C1 at the bottom of the distillation column, wherein
   at least a portion of the stream C2 is treated with an amount of acid such that pH of the stream C2 is adjusted to less than 6.4, then recycled to the reactor of Stage (i)(a).

2. The process of claim 1, wherein pH of the stream C2 is adjusted to less than pH 6.0.

3. The process of claim 1, wherein the treatment with the acid is carried out at a temperature of between about 20 and about 70° and at a pressure of between about 0.5 and about 4 bar absolute.

4. The process of claim 3, wherein the treatment with the acid is carried out at a temperature of between about 40 and about 60° C.

5. The process of claim 3, wherein the treatment with the acid is carried out at a pressure of between about 0.5 and about 2 bar absolute.

6. The process of claim 1, wherein the aqueous stream C2 contains from about 0.1 to about 20% $CO_2$, from about 1 to about 15% $NH_3$, and from about 0.1 to 10% reactant carrying a carbonyl group.

7. The process of claim 6, wherein the aqueous stream C2 contains from about 0.5 to about 5% $CO_2$.

8. The process of claim 6, wherein the aqueous stream C2 contains from about 1 to about 6% $NH_3$.

9. The process of claim 6, wherein the aqueous stream C2 contains from about 0.1 to 5% reactant carrying a carbonyl group.

10. The process of claim 1, wherein entire amount of the stream C2 is subjected to the treatment with the acid.

11. The process of claim 1, wherein the reactant carrying a carbonyl group is methyl ethyl ketone.

12. The process of claim 1, wherein the acid employed in the treatment of the stream C2 is an acid with a $pK_a$ of less than 6.3.

13. The process of claim 12, wherein the acid employed in the treatment of the stream C2 is an acid with a $pK_a$ of less than 5.

14. The process of claim 1, wherein the working solution comprises an acid what is used in the treatment of the stream C2.

15. The process of claim 14, wherein the working solution employed comprises an aqueous solution of acetamide and of acetic acid, and the acid used in the treatment of the stream C2 is acetic acid.

16. The process of claim 14, wherein the working solution employed comprises an aqueous solution of cacodylic acid and ammonium cacodylate, and the acid used in the treatment of the stream C2 is cacodylic acid.

17. The process of claim 1, which further comprises hydrolyzing the azine separated from the working solution to hydrazine, and recovering and recycling the reactant carrying a carbonyl group to the reactor for the synthesis of the azine.

* * * * *